United States Patent
Danielsson et al.

(10) Patent No.: US 10,143,417 B2
(45) Date of Patent: Dec. 4, 2018

(54) X-RAY IMAGING FOR ENABLING ASSESSMENT OF SCOLIOSIS

(71) Applicant: Prismatic Sensors AB, Stockholm (SE)

(72) Inventors: Mats Danielsson, Taby (SE); Xuejin Liu, Taby (SE); Martin Sjolin, Stockholm (SE)

(73) Assignee: PRISMATIC SENSORS AB, Stockholm (SE)

( * ) Notice: Subject to any disclaimer, the term of this patent is extended or adjusted under 35 U.S.C. 154(b) by 0 days.

(21) Appl. No.: 15/430,880

(22) Filed: Feb. 13, 2017

(65) Prior Publication Data
US 2017/0340268 A1    Nov. 30, 2017

Related U.S. Application Data

(63) Continuation of application No. PCT/SE2016/050497, filed on May 30, 2016.

(51) Int. Cl.
*A61B 6/00* (2006.01)
*A61B 5/00* (2006.01)
*A61B 6/03* (2006.01)

(52) U.S. Cl.
CPC .......... *A61B 5/4561* (2013.01); *A61B 6/032* (2013.01); *A61B 6/4241* (2013.01); *A61B 6/505* (2013.01); *A61B 6/5217* (2013.01)

(58) Field of Classification Search
None
See application file for complete search history.

(56) References Cited

U.S. PATENT DOCUMENTS

| 6,023,495 | A | * | 2/2000 | Adler | A61B 6/032 378/4 |
| 7,095,881 | B2 | | 8/2006 | Lelong et al. | |
| 8,183,535 | B2 | | 5/2012 | Danielsson et al. | |
| 2003/0215122 | A1 | * | 11/2003 | Tanaka | A61B 5/1075 382/128 |
| 2010/0084564 | A1 | * | 4/2010 | Moody | G01T 1/2018 250/366 |
| 2011/0021914 | A1 | | 1/2011 | Zheng et al. | |

(Continued)

FOREIGN PATENT DOCUMENTS

| WO | 2011/098895 A2 | 8/2011 |
| WO | 2011/0988895 A2 | 8/2011 |

OTHER PUBLICATIONS

Engelke et al (Clinical use of quantitative computed tomography and peripheral quantitative computer tomography in the management of osteoperosis in Adults: the 2007 ISCD official positions).*

(Continued)

*Primary Examiner* — Joel F Brutus
(74) *Attorney, Agent, or Firm* — Young & Thompson

(57) ABSTRACT

There is provided an arrangement (100) for enabling assessment of scoliosis. The arrangement (100) is configured to obtain at least one x-ray image by means of one or more photon-counting x-ray detectors. The arrangement (100) is further configured to determine at least one characteristic of the spine of a patient having possible scoliosis based on said at least one x-ray image obtained by means of the photon-counting x-ray detector(s) to enable assessment of scoliosis.

16 Claims, 11 Drawing Sheets

(56) References Cited

U.S. PATENT DOCUMENTS

| | | | |
|---|---|---|---|
| 2014/0303522 A1* | 10/2014 | Akimoto | A61B 5/4561 600/594 |
| 2015/0282774 A1 | 10/2015 | Lee et al. | |
| 2015/0305696 A1* | 10/2015 | Yamakawa | A61B 6/14 378/19 |
| 2015/0313566 A1* | 11/2015 | Diers | G06T 7/74 378/63 |

OTHER PUBLICATIONS

Taguchi, et al., "Vision 20/20: Single Photon Counting X-Ray Detectors in Medical Imaging," Medical Physics, vol. 40, No. 10, 2013, pp. 1-19.

Wang, et al., "Material Separation in X-Ray CT with Energy Resolved Photon-Counting Detectors," Medical Physics, vol. 38, No. 3, 2011, pp. 1534-1546.

Francke, et al., "Dose Reduction in Medical X-Ray Imaging Using Noise Free Photon Counting," Nuclear Instruments and Methods in Physics Research, vol. 471, No. 1, 2001, pp. 85-87.

Lundqvist, et al., "Evaluation of a Photon-Counting X-Ray Imaging System," IEEE Transactions on Nuclear Science, vol. 48, No. 4, 2001, pp. 1530-1536.

Damet, et al., "Occupational and Patient Exposure as well as Image Quality for Full Spine Examinations with the EOS Imaging System," Medical Physics, vol. 41, No. 6, 2014, pp. 1-12.

Written Opinion and International Search Report issued in Application No. PCT/SE2016/050497, dated Mar. 7, 2017.

Anderson, S. M. et al., "Spinal Curves and Scoliosis," Radiologic Technology, vol. 79, No. 1, Sep./Oct. 2007, pp. 44-65.

Delorme, S. et al., "Assesment of the 3-D Reconstruction and High-Resolution Geometrical Modeling of the Human Skeletal Trunk from 2-D Radiographic Images," IEEE Transactions on Biomedical Engineering, vol. 50, No. 8, Aug. 2003, pp. 989-998.

Kuklo, T. R. et al., "Reliability Analysis for Digital Adolescent Idiopathic Scoliosis Measurements," Journal of Spinal Disorders & Techniques, vol. 18, No. 2, Apr. 2005, pp. 152-159.

Göçen et al., "Effect of Rotation on Frontal Plane Deformity in Idiopathis Scoliosis," Orthopedics, vol. 24, No. 3, Mar. 2001, pp. 265-268.

Malfair, D. et al., "Radiographic Evaluation of Scoliosis: Review," American Journal of Roentgenology, vol. 194, Mar. 2010, pp. S8-S22.

Pruijs, J. E. H. et al., "Variation in Cobb Angle Measurements in Scoliosis," Skeletal Radiol, vol. 23, 1994, pp. 517-520.

Morrissy, R. T. et al., "Measurement of the Cobb Angle on Radiographs of Patients Who Have Scoliosis," The Journal of Bone and Joint Surgery, vol. 72-A, No. 3, Mar. 1990, pp. 320-327.

Tauchi, R. et al., "Reliability Analysis of Cobb Angle Measurements of Congenital Scoliosis Using X-Ray and 3D-CT Images," European Journal Orthopaedic Surgery Traumatology, vol. 26, 2016, pp. 53-57.

Le, H. Q. et al., "Radiation Dose Reduction Using a CdZnTe-Based Computed Tomography System: Comparison to Flat-Panel Detectors," Medical Physics, vol. 37, No. 3, Mar. 2010, pp. 1225-1236.

Alvarez, R. E. et al., "Energy-Selective Reconstructions in X-Ray Computerized Tomography," Physics in Medicine and Biology, vol. 21, No. 5, 1976, pp. 733-744.

Lundqvist, M. et al., "Evaluation of a Photon-Counting X-Ray Imaging System," IEEE Transaction on Nuclear Science, vol. 48, No. 4, Aug. 2001, pp. 1530-1536.

Chmeissani, M. et al., "First Experimental Tests with a Medipix2 Readout Chip," IEEE Transactions on Nuclear Science, vol. 51, No. 5, Oct. 2004, pp. 2379-2385.

Jacobson, B., "Dichromatic Absorption Radiography. Dichromography," Acta Radiologica, vol. 39, No. 6, Jun. 1953, pp. 437-452.

Lehmann, L. A. et al., "Generalized Image Combinations in Dual KVP Digital Radiography," Medical Physics, vol. 8, No. 5, Sep./Oct. 1981, pp. 659-667.

Johns, P. C. et al., "Theoretical Optimization of Dual-Energy X-Ray Imaging with Application to Mammography," Medical Physics, vol. 12, No. 3, May/Jun. 1985, pp. 289-296.

Taguchi K. and Iwanczyk J. S., "Single proton counting x-ray detectors in medical imaging", Medical Physics (2013), nr. 10, vol. 40, pp. 1-19; abstract; cols. 1-2.

Wang X. et al., "Material separation in x-ray CT with energy resolved photon-counting detectors", Medical Physics (2011), nr. 3, vol. 38, pp. 1534-1546; abstract.

Francke T. et. ai., "Dose reduction in medical X-ray imaging using noise free photon counting", Nuclear Instruments and Methods in Physics Research (2001), nr. 1, vol. 471, pp. 85-87; abstract; col. 1.

Lundqvist M. et. ai., "Evaluation of a photon-counting x-ray imaging system", IEEE Transactions on nuclear science (2001), nr. 4, vol. 48, pp. 1530-1536; abstract; cols. 1-4.

Damet J. et. ai., "Occupational and patient exposure as well as image quality for full spine examination with the EOS imaging system", Medical Physics (2014), nr. 6, vol. 41, pp. 1-12; abstract; p. 11, col. 1.

International Search Report issued in Application No. PCT/SE2016/050497, dated Mar. 7, 2017.

* cited by examiner

X-RAY IMAGING FOR ENABLING ASSESSMENT OF SCOLIOSIS

TECHNICAL FIELD

The proposed technology relates to x-ray imaging for enabling assessment of scoliosis, and more particularly to an arrangement for enabling assessment of scoliosis, and an x-ray imaging system comprising such an arrangement, a method for enabling assessment of scoliosis, and a corresponding computer program and computer-program product and apparatus.

BACKGROUND

Scoliosis is a medical condition where the spine has a complex three-dimensional (3D) deformity. It is generally characterized by a lateral deviation of the spine, accompanied by an axial rotation of the vertebrae, deformation of the rib cage, and possibly of the pelvis. When observed on a two-dimensional (2D) posteroanterior (PA) or anteroposterior (AP) radiographic image (images obtained while the patient stands in the upright position and the x-rays directly radiate to the backside or the front side of the patient), the spine is curved like a C or an S. Scoliosis may be the result of an underlying congenital or developmental osseous or neurologic abnormality, but in most cases the cause is unknown (idiopathic scoliosis). The high-risk group for scoliosis are adolescents and symptoms typically show during their grow spurts at the age of 13-14. In total 2% to 3% of the population are affected by scoliosis[1]. Progressive scoliosis, if left untreated, can result in significant deformity that can further cause dangerous complications such as heart and lung problems (i.e. shortness of breath).

Depending on the severity of the deformation, treatment of scoliosis can involve regular observation, bracing and/or surgery. The most common treatment is that the patients wear a brace that applies corrective forces through the soft tissue of the trunk, rib cage and pelvis. Surgical treatment usually involves correction of the scoliotic curves with pre-shaped metal rods anchored in the vertebrae with screws or hooks, and arthrodesis (bone fusion) of the intervertebral articulations of the instrumented segment of the spine [2].

For diagnosis, monitoring, therapeutic planning, and epidemiologic analysis of scoliosis, images of the spine are required. Imaging modalities such as radiography, computed tomography (CT) and magnetic resonance (MR) imaging are commonly used, where radiography plays the primary role.

In a 2D radiographic image, the degree of scoliosis is determined by estimating the curvature of the spine. The curvature is commonly quantified by the Cobb angle. When assessing the curve condition, the apical vertebra, which is the furthest deviated vertebra (FIG. 1 A), is first identified. The Cobb angle (FIG. 1 B) is defined as the angle between a line parallel to the upper end-plate of the most tilted vertebrae above the apical vertebrae and a line parallel to the lower end-plate of the most tilted vertebra below the apical vertebra (see FIG. 1). In the illustrative example of FIG. 1, two lines are drawn wherein one line parallel to the upper end-plate of the most tilted vertebrae above the apical vertebrae (A) while the other line parallel to the lower end-plate of the most tilted vertebra below the apical vertebra. The Cobb angle (B) is measured as illustrated.

In S-shaped scoliosis, where there are two contiguous curves, the lower end vertebra of the upper curve will represent the upper end vertebra of the lower curve. The angle can be measured manually or digitally, and the methods have been found to be equally reliable[3]. The Scoliosis condition is defined as a lateral spinal curvature with a Cobb angle larger than 10°.

Using a measurement of the Cobb angle in a single 2D image as the only measurement of the degree of scoliosis has its limitations since it only reflects the curvature of the spine in a single plane. As a result, the actual Cobb angle might be up to 20% greater than that estimated from the radiographs[4]. A total error of 2°-7° can also be expected in the Cobb angle assessment due to the variations in radiographic acquisitions and measurement error[5]. Moreover, intra-observer variation by 5°-10° in the Cobb angle measurement has been reported, and the inter-observer variation is even greater[6,7]. Despite these drawbacks, measurement of the Cobb angle is still the gold standard when assessing the curve severity and the risk of curve progression in scoliosis patients.

CT or MR imaging is performed when the radiography alone is inadequate to identify an underlying cause of scoliosis. Although MR imaging is radiation-free, its performance is limited for cases with metal implants. Clinically, the use of CT is mandatory in cases of a complex osseous deformity. In addition to radiography, CT images of scoliosis provide information about the extent of rotation of the spine, segmentation defects, and detection of bony spur in diastomatomyelia and associated congenital anomalies of ribs, scapula and pelvis. Cross-sectional CT images are useful for guiding surgical treatment and evaluating post-operative complications, and 3D CT can provide more detailed images of the anterior and posterior components of the malformed vertebrae. Also, CT images can be used to assess the traditional Cobb angle [8].

Meanwhile, the radiation dose during the x-ray imaging of patients with scoliosis is a major concern, especially for CT scanning, since adolescents, who are the high-risk group of scoliosis, also have higher sensitivity to x-ray radiation. Many "radiation free" methods and systems for estimating the degree of scoliosis have therefore been proposed. For instance, in U.S. Pat. App. No. 20140303522, an evaluation system a using 3D position sensor system to capture the uneven state of the body surface is disclosed. The downside of the proposed system is that it cannot perform the estimation of the Cobb angle or the inner condition of the deformed spine. In U.S. Pat. App. No. 20110021914, a 3D ultrasound imaging system for assessing scoliosis is disclosed. The solution is composed of an ultrasound scanner, a spatial sensor and a software module. The usability of the solution is however limited by its operational complexity, the limited dimension of ultrasound scanner and the poor image quality of bone in ultrasonic images. Many protocols for minimization and optimization of the radiation dose during imaging of scoliosis have been proposed. For instance, the company "EOS® Imaging" provides an imaging system that acquires low-dose whole-body radiographic images at two vertical directions at the same time. The detector/source pairs are positioned with a fixed relative angle between each other. 3D images of the spine can be reconstructed from these two unique low-dose images, with no additional radiation. Due to the sensitivity of patient movement, a unique scanner is required for acquiring the two images.

There is thus a general need for improvements for enabling assessment of scoliosis.

SUMMARY OF THE INVENTION

It is an object to provide an arrangement for enabling assessment of scoliosis.

It is another object to provide an x-ray imaging system comprising such an arrangement.

It is also an object to provide a method for enabling assessment of scoliosis.

Another object is to provide a corresponding computer program and computer-program product.

Yet another object is to provide an apparatus for enabling assessment of scoliosis.

These and other objects are met by embodiments of the proposed technology.

According to a first aspect, there is provided an arrangement for enabling assessment of scoliosis. The arrangement is configured to obtain at least one x-ray image by means of one or more photon-counting x-ray detectors. The arrangement is further configured to determine at least one characteristic of the spine of a patient having possible scoliosis based on said at least one x-ray image obtained by means of the photon-counting x-ray detector(s) to enable assessment of scoliosis.

According to a second aspect, there is provided an x-ray imaging system comprising such an arrangement.

According to a third aspect, there is provided a method for enabling assessment of scoliosis. The method comprises obtaining at least one x-ray image by means of one or more photon-counting x-ray detectors, and determining at least one characteristic of the spine of a patient having possible scoliosis based on said at least one x-ray image obtained by means of the photon-counting x-ray detector(s) to enable assessment of scoliosis.

According to a fourth aspect, there is provided a computer program comprising instructions, which when executed by a processor, causes the processor to:
- access at least one photon-counting-based x-ray image; and
- determine at least one characteristic of the spine of a patient having possible scoliosis based on said at least one photon-counting based x-ray image.

According to a fifth aspect, there is provided a computer program product comprising a computer-readable storage medium carrying the computer program of the fourth aspect.

According to a sixth aspect, there is provided an apparatus for enabling assessment of scoliosis. The apparatus comprises an input module for obtaining at least one x-ray image by means of one or more photon-counting x-ray detectors. The apparatus also comprises a determining module for determining at least one characteristic of the spine of a patient having possible scoliosis based on said at least one x-ray image obtained by means of the photon-counting x-ray detector(s) to enable assessment of scoliosis.

In this way, improved assessment of scoliosis is allowed in an efficient manner.

Other advantages will be appreciated when reading the detailed description.

BRIEF DESCRIPTION OF THE DRAWINGS

The embodiments, together with further objects and advantages thereof, may best be understood by making reference to the following description taken together with the accompanying drawings, in which.

DETAILED DESCRIPTION OF THE INVENTION

Figure 1:
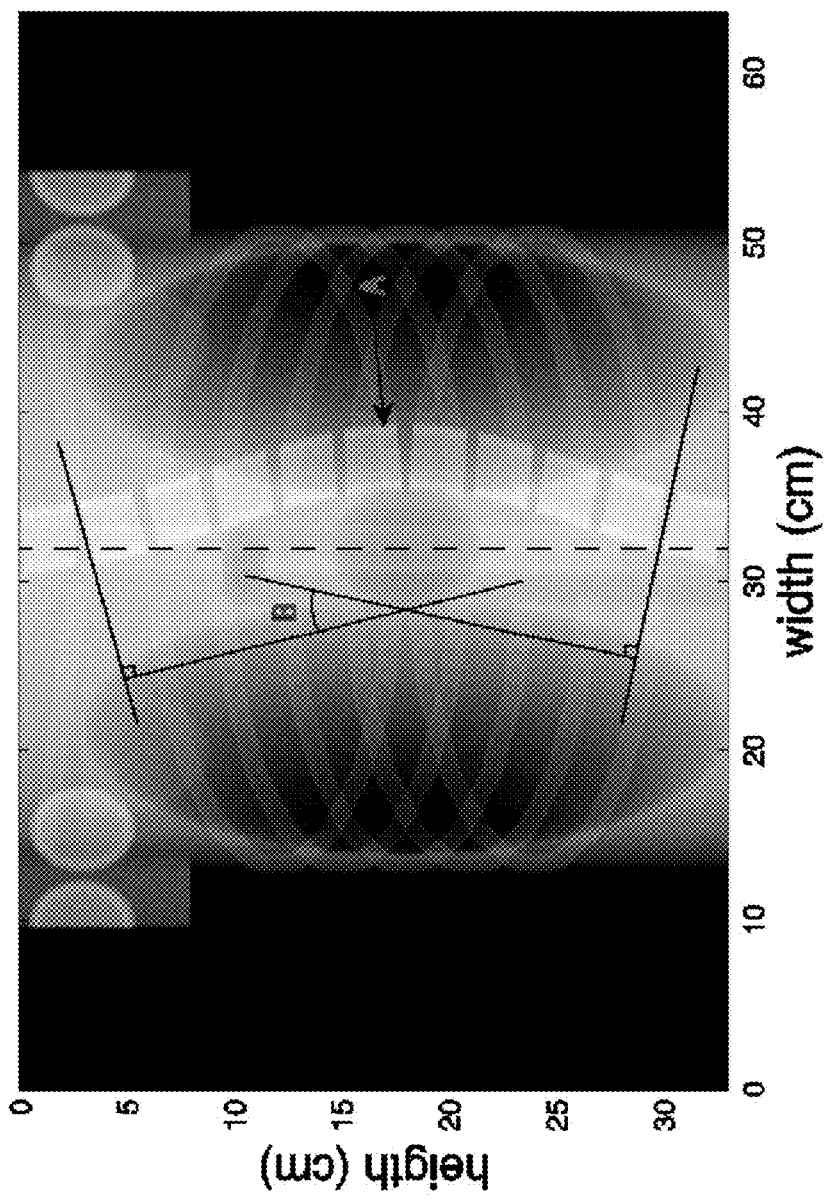
FIG. 1 is a schematic diagram illustrating an example of a simulated PA radiograph of a C-shaped scoliosis.

The inventors have recognized that the possible dose reduction for scoliosis imaging when using today's x-ray imaging systems is limited by the use of energy-integrating detectors. An energy-integrating detector integrates the electric charges produced by all the interacting x-rays in a detector pixel during a given period of time and outputs a signal proportional to the total amount of produced charges. Energy integrating detectors have at least the following limitations:

1) Energy-integrating detectors naturally place more weight to high-energy x-rays, which does not optimally utilize the contrast information carried in the detected x-rays (tissue contrast is higher for low-energy x-rays).
2) Electronic noise is integrated into the signals. In low-exposure applications or when imaging obese patients, electronic noise can have a significant impact on image quality.
3) In CT, images reconstructed with data from energy-integrating detectors suffer from beam hardening artifacts that degrade the diagnostic accuracy.

Therefore, there is provided an efficient arrangement for enabling assessment of scoliosis. The arrangement is configured to obtain at least one x-ray image by means of one or more photon-counting x-ray detectors. The arrangement is further configured to determine at least one characteristic of the spine of a patient having possible scoliosis based on said at least one x-ray image obtained by means of the photon-counting x-ray detector(s) to enable assessment of scoliosis.

Assessment of scoliosis typically includes assessing the curvature of the spine and/or other characteristics of the spine.

By way of example, the arrangement may be seen as a decision support system for allowing a doctor or other schooled practitioners to perform a conclusive assessment of scoliosis based on the information regarding the curvature of the spine and/or other characteristics of the spine.

For example, the arrangement is implemented as a dedicated scoliosis screening system.

Alternatively, the arrangement may be implemented as part of an x-ray imaging system such as a CT system.

In a first set of examples, the at least one x-ray image includes one or more 2D projection images.

For example, the arrangement may be configured to determine at least one characteristic of the spine by 2D positioning of the spine based on at least one 2D projection image.

Alternatively, the arrangement may be configured to determine at least one characteristic of the spine by 3D positioning of the spine based on a set of coupled 2D projection images with known relative orientation.

For the first set of examples, the arrangement may thus be based on a projection radiography source-detector system.

For the first set of examples, the arrangement may also be based on two or more coupled projection radiography source-detector systems.

In a second set of examples, the at least one x-ray image includes one or more 2D tomographic images.

For example, the arrangement may be configured to determine at least one characteristic of the spine by 2D positioning of the spine based on at least one 2D tomographic slice image.

Alternatively, the arrangement may be configured to determine at least one characteristic of the spine by 3D positioning of the spine based on a set of 2D tomographic slice images.

In a third set of examples, the at least one x-ray image includes one or more 3D tomographic images.

For example, the arrangement may be configured to determine at least one characteristic of the spine by 3D positioning of the spine based on 3D tomographic images.

For the third set of examples, the arrangement may be based on a Computed Tomography system.

The characteristic(s) of the spine may involve one or more important features.

By way of example, the at least one characteristic of the spine may include the Cobb angle.

For example, the at least one characteristic of the spine may include the maximal tilted angle in 3D, i.e. the Cobb angle as seen from the direction where it is maximal.

Alternatively, or as a complement, the at least one characteristic of the spine includes an indication of the apical vertebra.

Alternatively, or as a complement, the at least one characteristic of the spine includes an indication of a significant vertebrae, e.g. the vertebra with the maximal tilt.

Alternatively, or as a complement, the at least one characteristic of the spine includes an indication of the vertebral rotation.

In a particular example, the arrangement may be configured to obtain at least one x-ray image by means of one or more photon-counting and energy resolving x-ray detectors. The arrangement is thus configured to perform material decomposition and produce an image containing only bone, facilitating the identification of the form of the spine, and determine at least one characteristic of the spine based on this image.

It will be appreciated that the methods and arrangements described herein can be implemented, combined and re-arranged in a variety of ways.

For example, embodiments may be implemented in hardware, or in software for execution by suitable processing circuitry, or a combination thereof.

The steps, functions, procedures, modules and/or blocks described herein may be implemented in hardware using any conventional technology, such as discrete circuit or integrated circuit technology, including both general-purpose electronic circuitry and application-specific circuitry.

Alternatively, or as a complement, at least some of the steps, functions, procedures, modules and/or blocks described herein may be implemented in software such as a computer program for execution by suitable processing circuitry such as one or more processors or processing units.

Examples of processing circuitry includes, but is not limited to, one or more microprocessors, one or more Digital Signal Processors (DSPs), one or more Central Processing Units (CPUs), video acceleration hardware, and/or any suitable programmable logic circuitry such as one or more Field Programmable Gate Arrays (FPGAs), or one or more Programmable Logic Controllers (PLCs).

It should also be understood that it may be possible to re-use the general processing capabilities of any conventional device or unit in which the proposed technology is implemented. It may also be possible to re-use existing software, e.g. by reprogramming of the existing software or by adding new software components.

Figure 2:
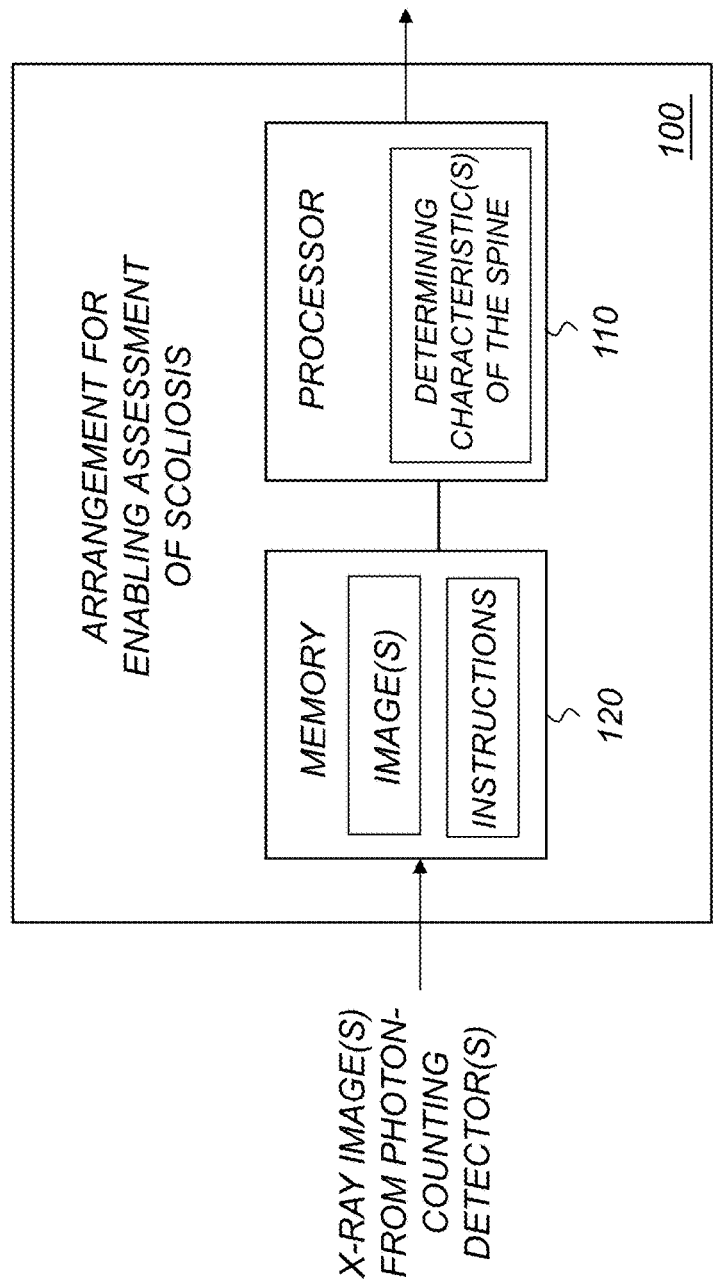
FIG. 2 is a schematic block diagram illustrating an example of an arrangement for enabling assessment of scoliosis according to an embodiment.

FIG. 2 is a schematic block diagram illustrating an example of an arrangement 100 for enabling assessment of scoliosis. In this particular example, the arrangement 100 comprises a processor 110 and a memory 120. The arrangement receives one or more x-ray images obtained from one or more photon-counting x-ray detectors. The x-ray images may be stored in the memory 120. The memory 120 also comprises instructions executable by the processor 110, whereby the processor is operative to enable assessment of scoliosis and determine characteristic(s) of the spine.

In particular, there is provided a computer program comprising instructions, which when executed by a processor, causes the processor to:

access at least one photon-counting-based x-ray image; and determine at least one characteristic of the spine of a patient having possible scoliosis based on said at least one photon-counting based x-ray image.

It is also possible to provide a solution based on a combination of hardware and software. The actual hardware-software partitioning can be decided by a system designer based on a number of factors including processing speed, cost of implementation and other requirements.

Figure 3:
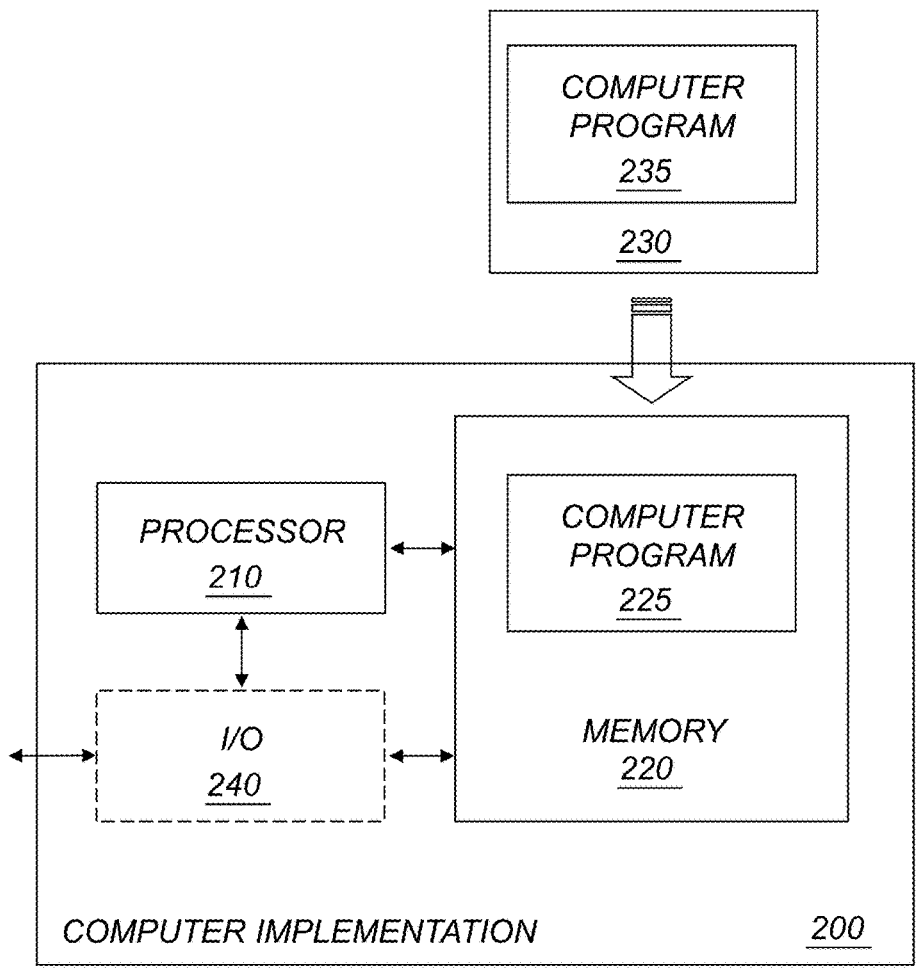
FIG. 3 is a schematic diagram illustrating an example of a computer-implementation according to an embodiment.

FIG. 3 is a schematic diagram illustrating an example of a computer-implementation 200 according to an embodiment. In this particular example, at least some of the steps, functions, procedures, modules and/or blocks described herein are implemented in a computer program 225; 235, which is loaded into the memory 220 for execution by processing circuitry including one or more processors 210. The processor(s) 210 and memory 220 are interconnected to each other to enable normal software execution. An optional input/output device 240 may also be interconnected to the processor(s) 210 and/or the memory 220 to enable input and/or output of relevant data such as input parameter(s) and/or resulting output parameter(s).

The term 'processor' should be interpreted in a general sense as any system or device capable of executing program code or computer program instructions to perform a particular processing, determining or computing task.

The processing circuitry including one or more processors 210 is thus configured to perform, when executing the computer program 225, well-defined processing tasks such as those described herein.

The processing circuitry does not have to be dedicated to only execute the above-described steps, functions, procedure and/or blocks, but may also execute other tasks.

The proposed technology also provides a computer program product comprising a computer-readable storage medium carrying the computer program described herein.

By way of example, the software or computer program 225; 235 may be realized as a computer program product, which is normally carried or stored on a computer-readable medium 220; 230, in particular a non-volatile medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program may thus be loaded into the operating memory of a computer or equivalent processing device for execution by the processing circuitry thereof.

According to another aspect, there is provided an x-ray imaging system comprising such an arrangement.

Figure 4:
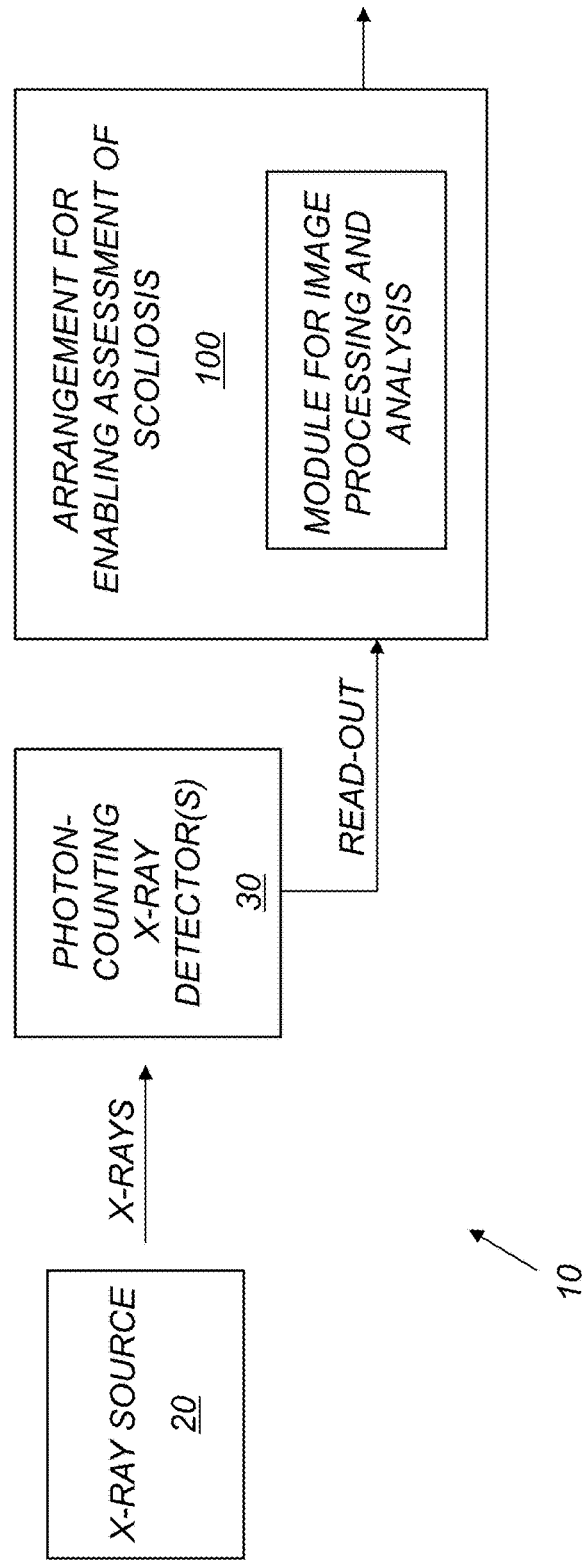
FIG. 4 is a schematic block diagram illustrating an example of an overall x-ray imaging system according to an embodiment.

FIG. 4 is a schematic block diagram illustrating an example of an overall x-ray imaging system. In this example, the x-ray imaging system 10 comprises an x-ray source 20, one or more photon-counting x-ray detectors 30 and an arrangement 100 for enabling assessment of scoliosis. By way of example, the arrangement 100 may be implemented as a processor-memory-based module for image processing and analysis configured for enabling assessment of scoliosis. There may be read-out circuitry integrated or associated with the x-ray detector(s) 30 for read-out of one or more photon-counting-based x-ray images. The image(s) is/are then transferred to the arrangement 100 for enabling assessment of scoliosis.

Figure 5:
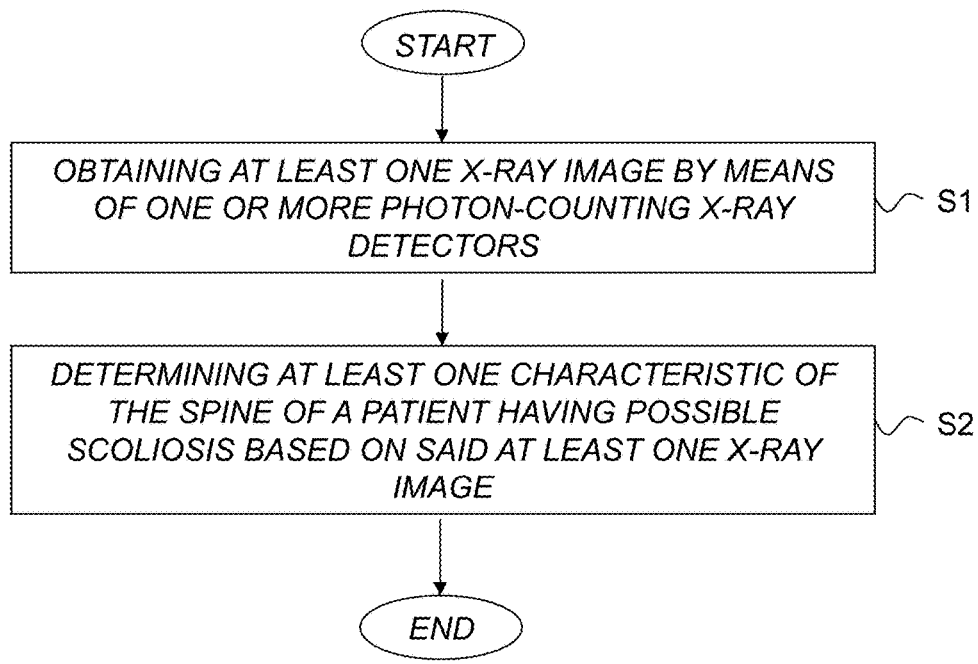
FIG. 5 is a schematic flow diagram illustrating an example of a method for enabling assessment of scoliosis according to an embodiment.

FIG. 5 is a schematic flow diagram illustrating an example of a method for enabling assessment of scoliosis. The method comprises:

S1: obtaining at least one x-ray image by means of one or more photon-counting x-ray detectors, and S2: determining at least one characteristic of the spine of a patient having possible scoliosis based on said at least one x-ray image obtained by means of the photon-counting x-ray detector(s) to enable assessment of scoliosis.

In the following, the proposed technology will be described with reference to a set of particular, non-limiting examples.

Photon-counting x-ray detectors are most commonly fabricated using solid-state semiconductors, i.e. silicon or CdTe/CZT. Incident x-ray photons are directly transferred to electrical pulses with pulse amplitudes proportional to the photon energies. For energy discriminating detectors, the pulse heights are then compared to a number of programmable thresholds in the readout circuits and classified according to pulse-height, which in turn is proportional to energy. By setting the minimal threshold above the noise floor, electronic noise, which is the major obstacle in the reduction of radiation dose for today's x-ray imaging systems, can be eliminated. It has been demonstrated that dose reductions up to 52.05% and 49.45% are achievable when using CZT detectors for iodine and hydroxyapatite imaging respectively, while maintaining the image quality[9]. For the simple imaging task of identifying the position of the spine, the dose can be reduced even further.

One benefit of using photon-counting detectors is the improved dose efficiency up to 40%-400% compared to a conventional integrating system [11,12].

Further, photon-counting detectors can be energy resolving, which enables spectral imaging and material basis decomposition (where materials are separated by their energy dependent attenuation). For scoliosis imaging, the material separation can be used to remove the surrounding tissue and presenting an image of the bone only, which can be helpful when visualizing the curvature of the spine.

These multi-energy images can be used for, for instance, dichromatic absorption radiography [13], in which high-Z materials such as iodine contrast agent can be visualized by image subtraction across the K edge. They can also be used to subtraction radiography to suppress unwanted contrast, allowing the materials of interest to be more apparent [14,15]. For example, bone shadows can be removed from chest images, allowing greater visualization of soft tissue structures. This could be beneficial in the diagnosis of complications of scoliosis such as heart and lung problems.

Photon-counting detectors have not been used for assessing scoliosis anywhere in the prior art.

Common for all proposed configurations is that a photon counting detector is used for x-ray imaging in the purpose of assessing scoliosis. Possible system configurations using photon-counting detectors for enabling assessment of scoliosis include, but are not limited to:

1) A Projection Radiography System

Figure 6:
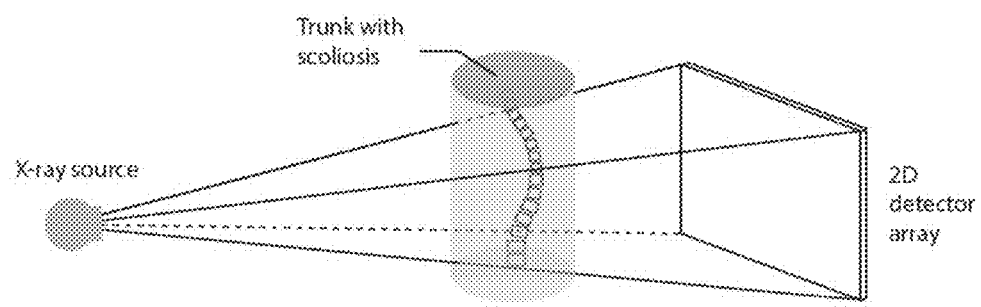
FIG. 6 is a schematic diagram illustrating an example of a system configuration using photon-counting detectors for enabling assessment of scoliosis.

FIG. 6 is a schematic diagram illustrating an example of a system configuration using photon-counting detectors for enabling assessment of scoliosis.

The system comprises a single x-ray source and an opposing 2D photon counting detector. The system can be used to acquire 2D projection images of the patient. If the projection angle is to be changed, then either the patient is moved or the source/detector system is moved.

2) Two Coupled Projection Radiography Systems

Figure 7:
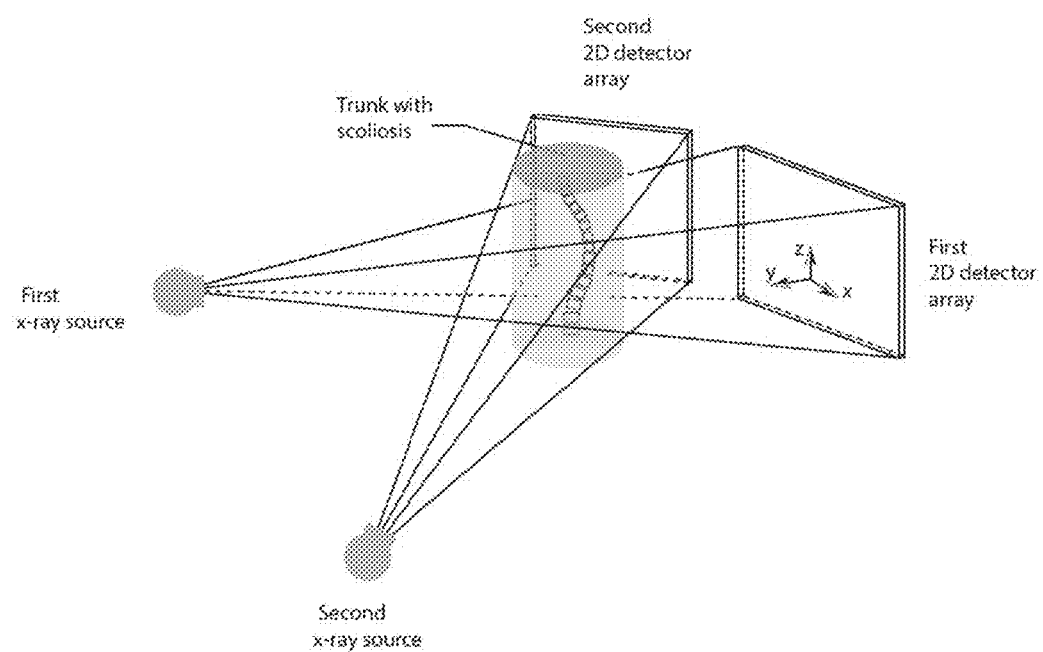
FIG. 7 is a schematic diagram illustrating another example of a system configuration using photon-counting detectors for enabling assessment of scoliosis.

FIG. 7 is a schematic diagram illustrating another example of a system configuration using photon-counting detectors for enabling assessment of scoliosis.

The system comprises two x-ray sources and two photon-counting detectors. The two source/detector systems take 2D projection images of the patient from two different directions simultaneously, which allows the system to find the position and orientation of the spine in 3D by means of a positioning procedure.

A positioning procedure could be any set of steps and/or actions that may be used to estimate a geometrical feature in the data set. For example, the curvature of the spine can be estimated by first determining the center of the spine for several image slices and then fitting a continuous curve to the estimated spine centers.

The described configuration may also have a flexible angle between two sources. For example, one source/detector is fixed while the other one can rotate around it.

3) A Computed Tomography (CT) System

Figure 8:
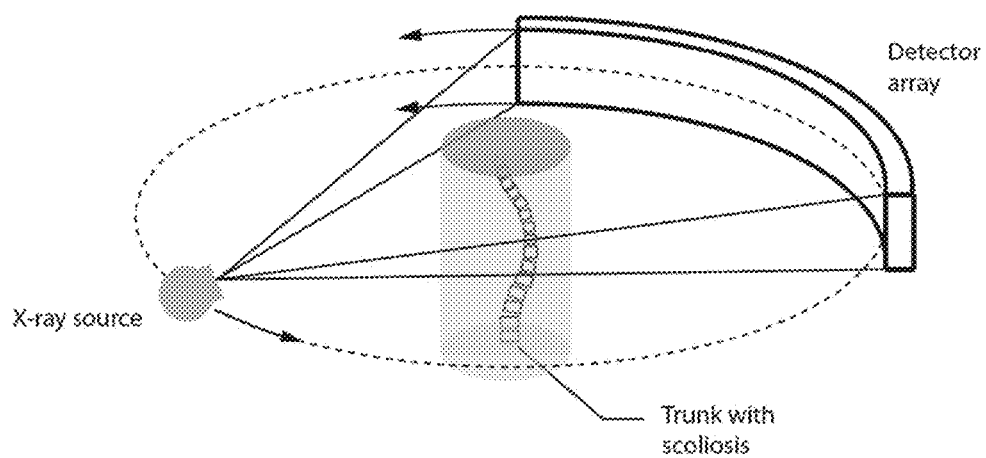
FIG. 8 is a schematic diagram illustrating yet another example of a system configuration using photon-counting detectors for enabling assessment of scoliosis.

FIG. 8 is a schematic diagram illustrating yet another example of a system configuration using photon-counting detectors for enabling assessment of scoliosis.

The system comprises an x-ray source and a photon counting detector mounted on a gantry that can be rotated with respect to a patient table. For example, the configuration may be based on a CT scanner equipped with photon-counting x-ray detectors.

By way of example, the detector assembly can have the general configuration as disclosed in U.S. Pat. No. 8,183,535 B2.

An example system may comprise a CT scanner with photon-counting detectors, which can acquire radiographic, tomographic, as well as 3D-CT images at much lower radiation dose than planar x-ray imaging machines or clinical CT systems. Also, the maximum curvature of the spine, as well as the tilt of the individual vertebra, can be automatically measured using the 3D image of the spine. Also, the doctor-preferred Cobb angle can be easily calculated. Moreover, bone images can be obtained through material decomposition technique that is only achievable by using photon-counting detectors with energy discrimination capability.

The above system configuration(s) can be operated in several different modes that acquire different types of image data, for example:

i) 2D projection images: The system can be used to acquire 2D images of the patient by keeping the gantry still and moving the patient using the table (which the patient lies on).

ii) Multiple 2D projection images: images can be acquired by rotating the gantry to different angles and acquiring 2D images with the gantry standing still. The different images will be coupled, i.e. the relative orientation known, since the orientation of the source and the detector with respect to the patient is well known, which allows 3D positioning of the spine in accordance with the system configuration 2).

iii) 2D Tomographic images: data can be acquired and used to find the position the spine in a 2D slice. In this mode of operation, the gantry is rotating and the patient table is still.

iv) Multiple 2D tomographic images: images can be acquired at different positions of the patient table. The orientation of the spine in 3D can be estimated from the position of the spine in the set of 2D slices by means of a positioning algorithm.

v) 3D tomographic images: can be acquired and used to find the position and orientation of the spine in 3D. In this mode of operation, the gantry is rotated and the patient table is translated. To enhance the spine when presenting the images, the background can be removed from the 3D data and 2D projection images, which only contain the spine, can be synthesized. The orientation of the spine in 3D can be estimated by means of a positioning algorithm.

At the initial diagnostic stage, when the Cobb angle is the most important feature when determining the severity of the deformity, the first and the second modes can be chosen.

When more accurate position of the deformed spine is demanded, the second, the forth and the last modes can be chosen, where the orientation of the spine in 3D can be obtained.

When more detailed tomographic images are needed, for instance, in the identification of an underlying cause or a surgery plan, the last three options can be used.

Also, the computed tomography system can be utilized to obtain the images similar to those obtained by the projection radiography configuration and the coupled projection radiography system. By using the CT as a 2D projection imager, the operator can choose to switch between the modes and e.g. first take a 2D image and then decide whether or not to proceed and take a second image. Since the first image is stored on the computer, the second image can be used together with the first to find the 3D curvature of the spine.

Also, since the gantry can be rotated to any position, it is possible to take a 2D image from the direction where the Cobb angle is assumed to be the largest based on the obtained 3D curvature of the spine.

Not only may photon counting detectors be used, but also several novel operation modes dedicated for scoliosis assessment can be used, which are not commonly used for CT systems, such as acquiring a 2D projection image, and/or multiple 2D projection images.

Examples of benefits of the proposed system include one or more of the following:

1) The photon counting operation allows imaging at ultra-low dose, which is essential for screening applications such as scoliosis assessment.
2) A CT system with a photon counting detector functions as a conventional CT and can therefore perform all the tasks of a conventional CT. Scoliosis imaging can therefore be performed without having a dedicated imaging system (such as the EOS system), thus becoming more available in the clinic.
3) Having the projection images acquired in a CT gantry allows for coupling of the data since the relative orientation of the angles at which the projection images were acquired are known. This allows for 3D positioning of the spine.
4) The patient is lying down, which is similar to the position the patient has during surgeries. This can avoid difference in Cobb angle assessment between imaging and surgery.

Using the example system configuration, radiographic images can be obtained at an arbitrary projection angles. The Cobb angle can be measured from the 2D images manually or digitally.

One or more radiographic images at different projection angles can be obtained by one exam by this example embodiment. For instance, the CT gantry rotates normally while the patient's bed moves, but only radiates and samples the imaged object at a set of chosen projection angles. The number of projection angles can be optimized in accordance with the purpose of the exam. If two projection angles are chosen, as for the EOS® imaging system, similar data processing can be applied here. For more information on 3D geometric modeling, reference can be made, e.g. to the image processing method described in U.S. Pat. No. 7,095,881. 3D modeling can also be obtained for more than two projection angles. Also, 3D reconstruction methods similar to that disclosed in WO/2011/098895A2 can be applied.

Figure 9:
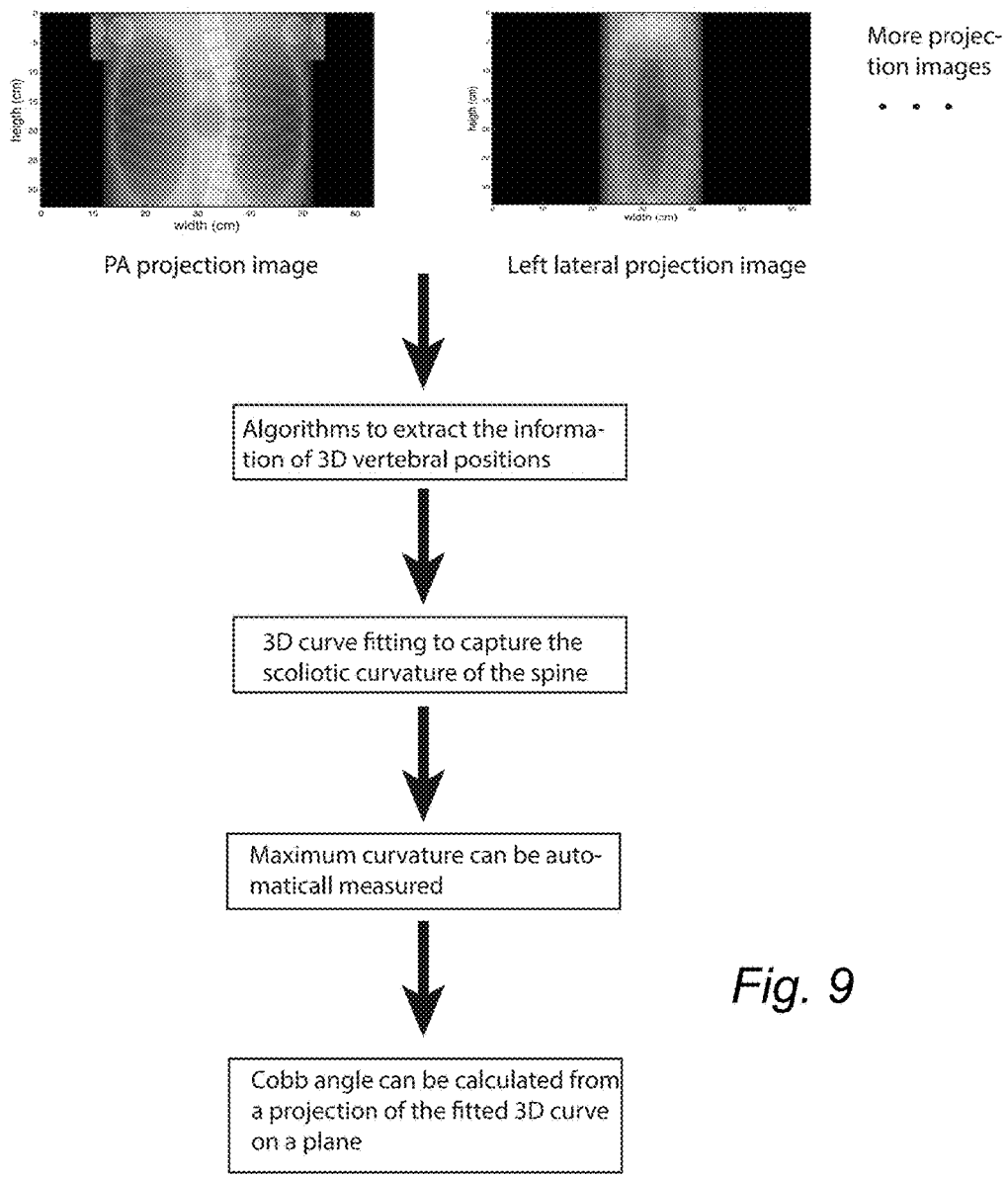
FIG. 9 is a schematic diagram illustrating an example of 3D curve fitting to assess the maximum curvature of the scoliotic spine as well as the Cobb angle from two or more radiographic images at different projection angles.

Also, it is possible to extract information of the maximum curvature of the spine from the obtained images. The vertebrae positions can be identified from two or more projective views of the spine and a 3D curve fitting can be used to capture the curvature of the spine, from which the maximum curvature of the spine can be assessed. This could be a more accurate figure-of-merit for the diagnosis of scoliosis since it exactly reflects the 3D deformity of the spine. Of course, the Cobb angle can also be easily calculated from a projection of the fitted 3D curve onto a plane. A schematic flow diagram of the proposed application is shown in FIG. 9.

Figure 10:
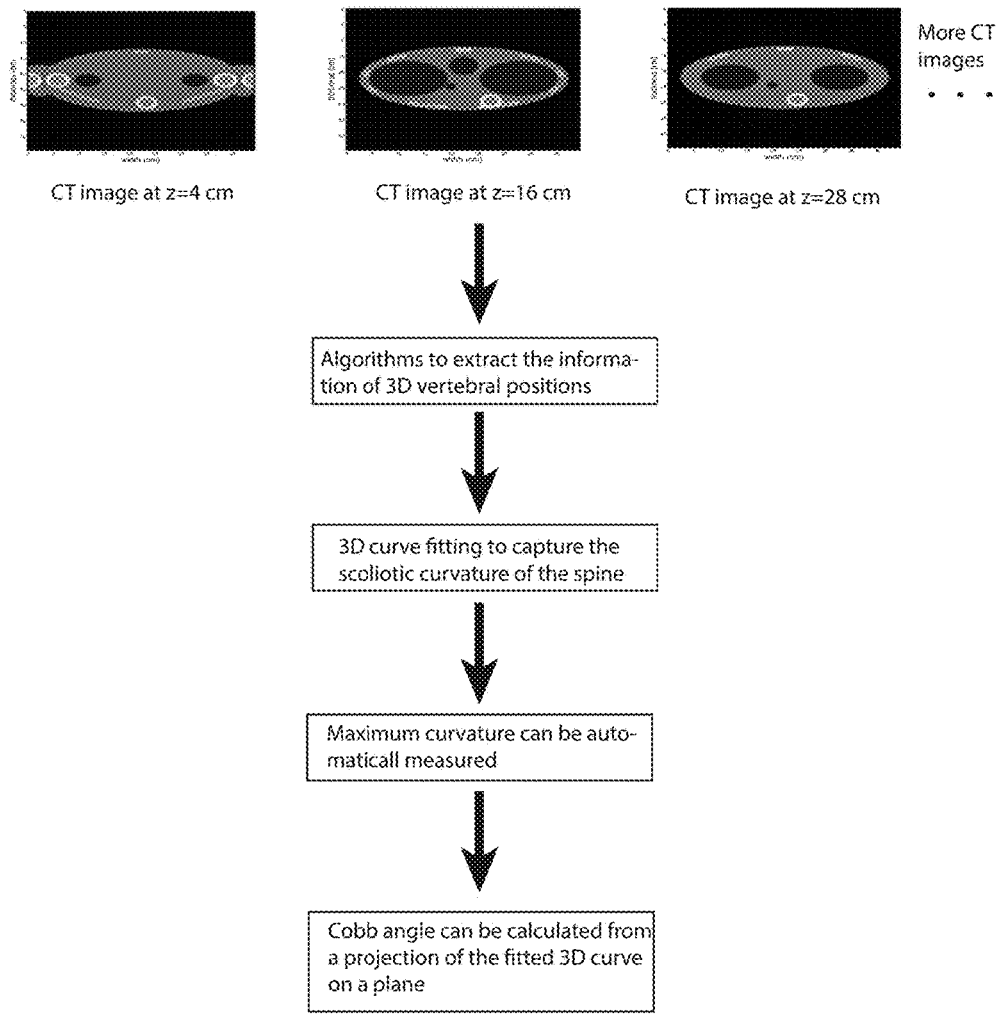
FIG. 10 is a schematic diagram illustrating an example of 3D curve fitting to assess the maximum curvature of the scoliotic spine as well as the Cobb angle from discretely sampled CT images along the z-direction of the spine.

In an example embodiment, the curvature of the spine can be discretely sampled since using a full spine CT for capturing the shape of the spine can be an excessive use of radiation. In the proposed method, tomographic images can be obtained at discrete locations (a finite number of positions, chosen by the operator) along the z-direction of the spine. The curvature of the spine can be estimated from this sub-set of a 2D projection since the curvature of the spine is usually smooth. These tomographic images together with their sampled z-positions can also be used for a 3D curve fitting of the curvature of the spine, from which the maximum curvature and the Cobb angle can be assessed. A schematic flow diagram of the proposed application is shown in FIG. 10.

All of the above mentioned applications can be achieved using modern clinical CT system, but at a much higher dose level than if a photon-counting detector is used. The following application is based on using a photon counting and an energy resolving detector. The photon counting and energy resolving detector can perform material decomposition and produce an image containing only bone, which makes the identification of the form of the spine easier. For more information on the material decomposition technique, reference can be made, e.g. to reference [10]. Whereas standard energy-integrating CT reconstructs an estimation of the linear attenuation coefficient for each voxel in the image, material decomposition techniques break down the content of each voxel into a set of materials, for example soft tissue, bone and lipid. By displaying only the bone in the image, the form of the spine will become clearer. A 3D bone image can also be obtained using volume rendering techniques.

The flow diagram or diagrams presented herein may be regarded as a computer flow diagram or diagrams, when performed by one or more processors. A corresponding apparatus may be defined as a group of function modules, where each step performed by the processor corresponds to a function module. In this case, the function modules are implemented as a computer program running on the processor.

The computer program residing in memory may thus be organized as appropriate function modules configured to perform, when executed by the processor, at least part of the steps and/or tasks described herein.

Figure 11:
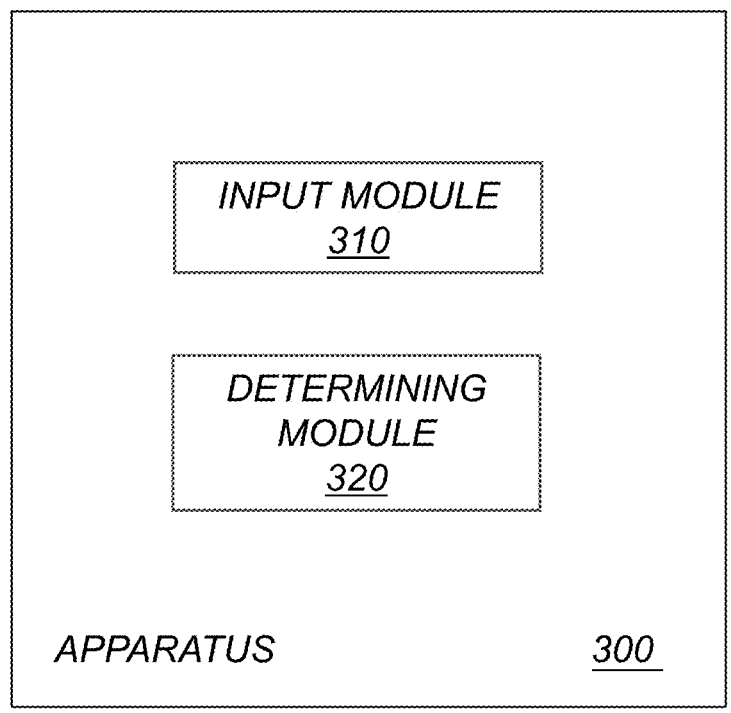
FIG. 11 is a schematic diagram illustrating an example of an apparatus for enabling assessment of scoliosis.

FIG. 11 is a schematic diagram illustrating an example of an apparatus for enabling assessment of scoliosis. The apparatus 300 comprises an input module 310 for obtaining at least one x-ray image by means of one or more photon-counting x-ray detectors. The apparatus 300 also comprises a determining module 320 for determining at least one characteristic of the spine of a patient having possible scoliosis based on said at least one x-ray image obtained by means of the photon-counting x-ray detector(s) to enable assessment of scoliosis.

Alternatively it is possible to realize the module(s) in FIG. 11 predominantly by hardware modules, or alternatively by hardware, with suitable interconnections between relevant modules. Particular examples include one or more suitably configured digital signal processors and other known electronic circuits, e.g. discrete logic gates interconnected to perform a specialized function, and/or Application Specific Integrated Circuits (ASICs) as previously mentioned. Other examples of usable hardware include input/output (I/O) circuitry and/or circuitry for receiving and/or sending signals. The extent of software versus hardware is purely implementation selection.

The embodiments described above are merely given as examples, and it should be understood that the proposed technology is not limited thereto. It will be understood by those skilled in the art that various modifications, combinations and changes may be made to the embodiments without departing from the present scope as defined by the appended claims. In particular, different part solutions in the different embodiments can be combined in other configurations, where technically possible.

PATENT REFERENCES

U.S. Pat. App. No. 20140303522
U.S. Pat. App. No. 20110021914
U.S. Pat. No. 7,095,881
U.S. Pat. No. 8,183,535B2
WO/2011/098895A2

OTHER REFERENCES

[1] Anderson, Susan M. "Spinal curves and scoliosis." *Radiologic technology* 79.1 (2007): 44-65.
[2] Delorme, Sébastien, et al. "Assessment of the 3-D reconstruction and high-resolution geometrical modeling of the human skeletal trunk from 2-D radiographic images." *Biomedical Engineering, IEEE Transactions on* 50.8 (2003): 989-998.
[3] Kuklo, Timothy R., et al. "Reliability analysis for digital adolescent idiopathic scoliosis measurements." *Journal of spinal disorders & techniques* 18.2 (2005): 152-159.
[4] Göçen, Sedat, and Hasan Havitçioglu. "Effect of rotation on frontal plane deformity in idiopathic scoliosis." *Orthopedics* 24.3 (2001): 265-268.
[5] Malfair, David, et al. "Radiographic evaluation of scoliosis: review." *American Journal of Roentgenology* 194.3_supplement (2010): S8-S22.
[6] Pruijs, J. E. H., et al. "Variation in Cobb angle measurements in scoliosis." *Skeletal radiology* 23.7 (1994): 517-520.
[7] Morrissy, RAYMOND T., et al. "Measurement of the Cobb angle on radiographs of patients who have scoliosis. Evaluation of intrinsic error." *J Bone Joint Surg Am* 72.3 (1990): 320-327.
[8] Tauchi, Ryoji, et al. "Reliability analysis of Cobb angle measurements of congenital scoliosis using X-ray and 3D-CT images." *European Journal of Orthopaedic Surgery & Traumatology* 26.1 (2016): 53-57.
[9] Le, Huy Q., Justin L. Ducote, and Sabee Molloi. "Radiation dose reduction using a CdZnTe-based computed tomography system: Comparison to flat-panel detectors." *Medical physics* 37.3 (2010): 1225-1236.
[10] Alvarez, Robert E., and Albert Macovski. "Energy-selective reconstructions in x-ray computerised tomography." *Physics in medicine and biology* 21.5 (1976): 733.
[11] Lundqvist, Mats, et al. "Evaluation of a photon counting X-ray imaging system."*Nuclear Science Symposium Conference Record,* 2000 *IEEE*. Vol, 1. IEEE, 2000.
[12] Chmeissani, M., et al. "First experimental tests with a CdTe photon counting pixel detector hybridized with a Medipix2 readout chip." Nuclear Science, IEEE Transactions on 51.5 (2004): 2379-2385.
[13] Jacobson, Bertil. "Dichromatic absorption radiography. Dichromography." *Acta Radiologica* 39.6 (1953): 437-452.
[14] Lehmann, L A., et al. "Generalized image combinations in dual KVP digital radiography." *Medical physics* 8.5 (1981): 659-667.
[15] Johns, Paul C., and Martin J. Yaffe. "Theoretical optimization of dual-energy x-ray imaging with application to mammography." *Medical physics* 12.3 (1985): 289-296.

The invention claimed is:
1. An x-ray imaging system, comprising:
an x-ray source;
one or more photon-counting and energy discriminating x-ray detectors, each said detector configured to transfer incident x-ray photons into electrical pulses with pulse amplitudes proportional to photon energies of the incident x-ray photons;

read-out circuitry integrated or associated with the photon-counting and energy discriminating x-ray detector or detectors, wherein the read-out circuitry is configured to compare the pulse amplitudes of the electrical pulses to a number of thresholds for classifying the electrical pulses according to pulse amplitude, wherein a minimal threshold of the read-out circuitry is set above a noise floor to reduce electronic noise, wherein the read-out circuitry is configured to read-out at least one x-ray image free of the photons with the electrical pulses below the minimal threshold; and a processor and a memory, the memory comprising instructions executable by the processor, whereby the processor is operative to:

i) perform material basis decomposition based on said at least one x-ray image whereby materials identified in said at least one x-ray image are separated by their energy dependent attenuation and tissue surrounding the spine is removed by image processing to produce an image containing only energy dependent attenuations indicating bone with energy dependent attenuations not indicating bone being removed from the resulting final x-ray image, facilitating the identification of a spine of a patient having scoliosis, and ii) from the final x-ray image containing only energy dependent attenuations indicating bone, determine at least one characteristic of the spine of the patient having scoliosis.

2. The x-ray imaging system of claim 1, wherein said at least one x-ray image includes one or more 2D projection images.

3. The x-ray imaging system of claim 2, wherein the processor is operative to determine at least one characteristic of the spine by 2D positioning of the spine based on at least one 2D projection image.

4. The x-ray imaging system of claim 2, wherein the processor is operative to determine at least one characteristic of the spine by 3D positioning of the spine based on a set of coupled 2D projection images with known relative orientation.

5. The x-ray imaging system of claim 2, wherein the x-ray imaging system is based on a projection radiography source-detector system.

6. The x-ray imaging system of claim 1, wherein said at least one x-ray image includes one or more 2D tomographic images.

7. The x-ray imaging system of claim 6, wherein the processor is operative to determine at least one characteristic of the spine by 2D positioning of the spine based on at least one 2D tomographic slice image.

8. The x-ray imaging system of claim 6, wherein the processor is operative to determine at least one characteristic of the spine by 3D positioning of the spine based on a set of 2D tomographic slice images.

9. The x-ray imaging system of claim 6, wherein the x-ray imaging system is based on at least two coupled projection radiography source-detector systems.

10. The x-ray imaging system of claim 1, wherein said at least one x-ray image includes one or more 3D tomographic images.

11. The x-ray imaging system of claim 10, wherein the processor is operative to determine at least one characteristic of the spine by 3D positioning of the spine based on 3D tomographic images.

12. The x-ray imaging system of claim 1, wherein said at least one characteristic of the spine includes the Cobb angle.

13. The x-ray imaging system of claim 12, wherein said at least one characteristic of the spine includes the maximal tilted angle in 3D, i.e. the Cobb angle as seen from a direction where it is maximal.

14. The x-ray imaging system of claim 1, wherein said at least one characteristic of the spine includes an indication of the apical vertebra.

15. The x-ray imaging system of claim 1, wherein said at least one characteristic of the spine includes an indication of a vertebra with a maximal tilt.

16. The x-ray imaging system of claim 1, wherein said at least one characteristic of the spine includes an indication of a vertebral rotation.

* * * * *